(12) United States Patent
Harold

(10) Patent No.: US 7,251,528 B2
(45) Date of Patent: Jul. 31, 2007

(54) TREATMENT OF VISION DISORDERS USING ELECTRICAL, LIGHT, AND/OR SOUND ENERGY

(75) Inventor: Thomas W. Harold, Chanhassen, MN (US)

(73) Assignee: ScyFIX, LLC, Chanhassen, MN (US)

( * ) Notice: Subject to any disclaimer, the term of this patent is extended or adjusted under 35 U.S.C. 154(b) by 0 days.

(21) Appl. No.: 10/565,544

(22) PCT Filed: Feb. 7, 2005

(86) PCT No.: PCT/US2005/003695

§ 371 (c)(1),
(2), (4) Date: Jan. 23, 2006

(87) PCT Pub. No.: WO2005/077452

PCT Pub. Date: Aug. 25, 2005

(65) Prior Publication Data

US 2006/0217783 A1 Sep. 28, 2006

Related U.S. Application Data

(60) Provisional application No. 60/542,724, filed on Feb. 6, 2004, provisional application No. 60/542,443, filed on Feb. 6, 2004, provisional application No. 60/542,768, filed on Feb. 6, 2004, provisional application No. 60/542,442, filed on Feb. 6, 2004.

(51) Int. Cl.
*A61N 1/00* (2006.01)

(52) U.S. Cl. .................................................. 607/41

(58) Field of Classification Search .............. 604/20, 604/22; 607/41, 53, 50
See application file for complete search history.

(56) References Cited

U.S. PATENT DOCUMENTS

| | | | |
|---|---|---|---|
| 4,614,193 A * | 9/1986 | Liss et al. .................... | 607/53 |
| 5,522,864 A | 6/1996 | Wallace et al. ............... | 607/53 |
| 5,935,155 A | 8/1999 | Humayun et al. ............ | 607/54 |
| 5,944,747 A | 8/1999 | Greenberg et al. ........... | 607/54 |
| 6,035,236 A | 3/2000 | Jarding et al. ............... | 607/53 |
| 6,101,411 A | 8/2000 | Newsome .................... | 604/20 |
| 6,154,671 A | 11/2000 | Parel et al. .................. | 604/20 |
| 6,275,735 B1 | 8/2001 | Jarding et al. ............... | 607/53 |
| 6,282,449 B1 | 8/2001 | Kamerling et al. .......... | 607/53 |
| 6,306,075 B1 | 10/2001 | Shadduck .................... | 600/12 |
| 6,990,377 B2 | 1/2006 | Gliner et al. ................ | 607/54 |
| 2003/0233137 A1 | 12/2003 | Paul, Jr. ..................... | 607/50 |
| 2004/0106965 A1 | 6/2004 | Chow ......................... | 607/54 |
| 2004/0176820 A1 | 9/2004 | Paul, Jr. ..................... | 607/53 |
| 2005/0004625 A1 | 1/2005 | Chow ......................... | 607/54 |
| 2005/0137649 A1 | 6/2005 | Paul, Jr. ..................... | 607/53 |

* cited by examiner

*Primary Examiner*—Mark Bockelman
(74) *Attorney, Agent, or Firm*—Nawrocki, Rooney & Sivertson, P.A.

(57) ABSTRACT

A non-invasive ocular therapy for vision disorders is provided. First and second electrodes of a direct current source are electrically contacted so as to deliver current to and/or about an area proximal one or more eyes of a subject. A direct electrical current of between about 1-800 microamps, at a resistance assumption of about 500 ohms, is generated between the electrodes for a preselected duration. Preferably, the direct electrical current is generated at a select frequency profile as a function of time, and with a carrier signal of about 10,000-12,000 hertz. Advantageously, the subject therapy is augmented via application of light energy to the eye(s), as well as by the application of infrasonic sound waves directly into eyes.

26 Claims, 10 Drawing Sheets

TWELVE WEEK STUDY - SNELLEN CHART RESULTS

| Patient # | Before Treatment OD | After Treatment OD | Before Treatment OS | After Treatment OS |
|---|---|---|---|---|
| 1 | 20/100 | 20/80 | 20/200 | 20/100-1 |
| 2 | | | | |
| 3 | | | 20/200 | 20/100-1 |
| 4 | | | 20/60 | 20/50-1 |
| 5 | 20/70+2 | 20/60+3 | 20/400 | 20/200+1 |
| 6 | 20/40-2 | 20/25-2 | 20/50-1 | 20/30-1+3 |
| 7 | 20/200 | 20/200 | 20/70 | 20/60 |
| 8 | 20/100 | 20/80 | 20/200 | 20/100 |
| 9 | 20/200 | 20/60-1 | 20/200 | 20/80-1 |
| 10 | 20/50 | 20/30+2 | 20/30 | 20/25+2 |
| 11 | 20/100 | 20/50+2 | 20/70 | 20/40+2 |
| 12 | 20/400 | 20/400 | 20/140 | 20/200 |
| 13 | 20/1000 | 20/400 | 20/400 | 20/200 |
| 14 | 20/20-2 | 20/15 | 20/20 | 20/15 |
| 15 | 20/20 | 20/20- | 20/40 | 20/30- |
| 16 | 20/50-1 | 20/50+1 | 20/250 | 20/200 |
| 17 | 20/30 | 20/25 | 20/200 | 20/60 |
| 18 | 20/400 | 20/400 | | |
| 19 | 20/200 | 20/200 | | |
| 20 | | | | |
| 21 | | | 20/50 | 20/40 |
| 22 | 20/80 | 20/60 | 20/50 | 20/40+2 |
| 23 | | | 20/40 | 20/40 |
| 24 | 20/50-2+2 | 20/50+2 | 20/25- | 20/30+4 |
| 25 | 20/50-1+3 | 20/60+2 | 20/1000 | 20/300 |
| 26 | 20/70 | 20/70 | 20/70 | 20/70 |
| 27 | 20/60 | 20/50 | 20/200 | 20/200 |
| 28 | 20/200 | 20/200 | 20/320 | 20/125-2 |
| 29 | | | 20/200 | 20/100+1 |
| 30 | | | 20/200-1 | 20/100+1 |
| 31 | 20/70+2 | 20/70-2 | | |
| 32 | 20/400 | 20/80-1 | | |
| 33 | | | 20/25-2 | 20/20-3 |
| 34 | 20/60 | 20/60-2+2 | | |
| 35 | | | 20/25-2 | 20/30+2 |
| 36 | | | 20/50 | 20/50-80 |
| 37 | 20/200 | 20/200+1 | | |
| 38 | | | 20/400 | 20/400 |
| 39 | 20/25+2 | 20/25-2 | 20/25+3 | 20/20-2 |
| 40 | 20/200+ | 20/70-1 | 20/400 | 20/400- |
| 41 | 20/400 | 20/200 | 20/80- | 20/80+1 |
| 42 | | | 20/20- | 20/20- |
| 43 | 20/400 | 20/200-1 | 20/400 | 20/400 |

TREATMENT OF VISION DISORDERS USING ELECTRICAL, LIGHT, AND/OR SOUND ENERGY

This is an international patent application filed under 35 U.S.C. §363 claiming priority under 35 U.S.C. §119(e)(1) of the following U.S. provisional patent applications: Appl. Ser. No. 60/542,768 filed Feb. 6, 2004; Appl. Ser. No. 60/542,442 filed Feb. 6, 2004; Appl. Ser. No. 60/542,443 filed Feb. 6, 2004; and, Appl. Ser. No. 60/542,724 filed Feb. 6, 2004.

TECHNICAL FIELD

This invention relates to the treatment of vision disorders (e.g., ocular disease), more particularly, the selective therapeutic application of energy, in the form of electrical, light and/or sound energy, to the eye(s).

BACKGROUND OF THE INVENTION

News and knowledge of vision disorders are on the rise. It is estimated that the lifetime costs for all people with vision impairment who were born in 2000 will total $2.5 billion (2003 dollars, see generally, Centers for Disease Control and Prevention, Economic Costs Associated with Mental Retardation, Cerebral Palsy, Hearing Loss, & Vision Impairment, United States, 2003, MMWR 2004;53:57-9). These costs include both direct and indirect costs. Direct medical costs, such as doctor visits, prescription drugs, and inpatient hospital stays, make up 6% of these costs. Direct nonmedical expenses, such as home modifications and special education, make up 16% of the costs. Indirect costs, which include the value of lost wages when a person dies early, cannot work, or is limited in the amount or type of work he or she can do, make up 77% of the costs. These estimates do not include other expenses, such as hospital outpatient visits, emergency department visits, and family out-of-pocket expenses. The actual economic costs of vision impairment are, therefore, even higher than what is generally reported.

The most common causes of vision impairment among adults in the United States are age-related macular degeneration (AMD), presbyopia, diabetic retinopathy, cataracts, and glaucoma. AMD affects the part of the retina that is responsible for sharp central vision and is the leading cause of legal blindness in the United States in persons over 65 years old. According to a March 1997 Review of Optometry Journal, 10% of our population over age 52 has AMD and 33% of individuals over age 75 have AMD. It is estimated that more than 13 million Americans now have AMD and that, by the time the Baby Boomers reach age 65, there will be over 30 million cases of AMD, almost 25% of our population over 65.

Presbyopia is a frustrating condition that begins to effect the "small print" visual acuity (i.e., blurred vision) of many individuals after they reach forty years of age. People find that they are unable to focus on the small print, and may develop headaches, eyestrain, or feel fatigued. Treatment typically involves buying inexpensive, "off-the-shelf" "reading glasses", surgery, or bi-focal contact lenses. It is believed that presbyopia occurs from a loss of elasticity or flexibility in the natural lens of the eye of those over forty years of age. During the age-related process, the proteins in the lens begin to make the lens harder, less elastic, with muscle fibers around the lens also effected. As the lens requires elasticity to focus up close, with a diminished or diminishing functionality, visual acuity is impacted.

Diabetic retinopathy is a common complication of diabetes in which the blood vessels in the retina break down, leak, or become blocked, leading to vision impairment. Cataracts are a clouding of the eye's lens, which is normally clear. Glaucoma is increased fluid and pressure within the eye that leads to enlargement of the eyeball. The risk of vision loss from many of these conditions can often be reduced if the condition is found early and treated.

Normal retinal cell function is a photochemical reaction converting light energy to an electrical impulse which travels to the brain and vision occurs. With AMD and other visual system diseases, diseased, inflamed retinal cells eventually lose cell function. Adenosine triphosphate (ATP) levels drop, protein synthesis drops, the electrical resistance goes up, and cell electricity potential goes down. Basically, the cells seem to go dormant for a time before they die. It is believed that, if electrical stimulation is provided to the cells before they die, blood vessel permeability is increased, a more normal cellular electrical potential will be achieved, the ATP levels will increase, protein synthesis will occur again, and normal cell metabolism will be restored.

Additionally, electrical stimulation appears to have a healing effect on the small blood vessels in the retina, promoting a more efficient delivery of nutrients to the retinal cells and a more efficient uptake of proteins that can accumulate on the retina. Thus, it is believed that microcurrent stimulation (i.e., the delivery of typically about less than 1,500 microamps) will help rejuvenate the cells in the retina to slow or stop degeneration of the eye due to AMD and the like. With the proper microcurrent stimulation wave form and therapy procedures, progressive vision disorders may be slowed or stopped in a large number of people suffering therefrom.

For example, Fedorov et al., U.S. Pat. No. 5,147,284, proposed to treat diseases of the optic nerve and retina by the application of a pulsed 3.5 magnetic flux, the magnetic field induction being from 0.1 T to 0.25 T. However the technique is invasive, requiring exposure of the posterior portion of the eyeball and optic nerve and introduction of the inducer into the orbit.

Liss et al., U.S. Pat. No. 4,614,193, proposed to treat glaucoma with the application of transcutaneous electrical stimulation, more particularly, the application of pulsed electrical current at a level less than 4 milliamperes, the pulse trains occurring at 12-20 kHz, amplitude modulated at 8-20 hz, and having a 3:1 duty cycle. Applying this waveform through electrodes positioned on the temple and on the ipsilateral hand, Liss et al. achieved an approximately 28% reduction in intraocular pressure in the treated eye. To the knowledge of the inventor, passage of electrical current through the eye, hereinafter "transocular electrical conduction," has been used in the art for the treatment of blindness disease, but has yet to be maximized as a vision disorder therapy, as for example, via the selection and/or combination of wave forms, power, duration, and frequencies.

Greenberg et al., U.S. Pat. No. 5,944,747, is generally directed to a method of focused phosphene generation through deeper intermediate retinal cellular electrical stimulation, to the exclusion of direct galleon cellular electrical stimulation, via the application of a long duration stimulation signal. Preferably, the long duration stimulation signal is a biphasic signal having a negative and positive phase pulse. It is further believed to be advantageous to make such biphasic pulses simulate cathodic monophasic pulses by using unequal amplitude phases.

It is suggested from Wallace et al., U.S. Pat. No. 5,522,864 that a direct current with a constant magnitude of 200 microamps has show positive effect in treating ocular disease including macular degeneration. Further, Jarding et al., U.S. Pat. Nos. 6,035,236 & 6,275,735, suggests that microcurrent stimulation, vis-a-vis the application of microcurrent approximate to an eye wherein the microcurrent has an amplitude of about 50-180 microamps and comprises a sweep wave microcurrent signal produced by a sweep wave signal generator, can improve vision in individuals suffering from additional "blindness" causing diseases, including retinitis pigmentosis. In these instances, the theory for improvement has to do with bringing energy to dormant photo-receptor cells. The inventor believes that the Wallace et al. effort is not expansive enough in both varying the power level and frequency selection/application duration, and further, that the Jarding et al. efforts are too broad in not specifying especially effective therapeutic frequencies. In the Jarding et al. case, this may be due to Jarding et al. attempting to treat a broad range of diseases including cancer which likely require technical considerations that are different from those implicated in overcoming vision disorders.

Thus there remains a need for an energy based treatment of vision disorders that maximizes therapeutic effect. Furthermore, it is believed advantageous to provide an energy based treatment that includes electrical, light and sound energy forms, alone or in select combination, to effectuate a therapeutic result in persons suffering from vision disorders. Further still, it is believed that improvements in transocular electrical conduction are achieved utilizing specific frequencies, wave forms, durations, and power algorithms in furtherance of maximizing subject visual efficacy.

SUMMARY OF THE INVENTION

It is a primary object of the present invention to provide an improved apparatus and method for the treatment of vision disorders.

It is another object of the present invention to provide a safe, improved, noninvasive method for the restoration of vision by treating the eye with transocular conduction of electrical current.

It is yet another object of the present invention to provide a safe, improved, noninvasive method for the restoration of vision by treating the eye with transocular conduction of electrical current supplemented by other energy forms, namely, light and/or sound energy.

These and other objects of the present invention are attained by a direct current generator that produces an amplitude modulated, low level, pulsed, direct current applied between electrodes, one placed on or proximal a closed eyelid and the other on a remote body location, e.g., a top of the subject's corresponding hand.

Blindness disease, as a species of vision disorder, is a debilitating ocular disease having hemorrhagic and exudative variants, both of which are susceptible to safe and efficient treatment by the subject invention. Treatment typically results in amelioration of the ophthalmoscopic manifestations of the disorder, and substantial restoration of central visual acuity. For the purpose of this disclosure, "blindness disease" means macular degeneration, presbyopia, retinitis pigmentosis and Stargardt's and may include one or more of: diabetic retinopathy, glaucoma, CMV-retinitis, Best's disease, macular dystrophy, optic neuritis, ischemic anterior optic neuritis, Usher's syndrome, Leber's congenital amaurosis, cone-rod dystrophy, cone dystrophy, choroideremia and gyrate atrophy, central retinal artery occlusion, central retinal vein occlusion, branch retinal artery occlusion, branch retinal vein occlusion, central serous chorioretinopathy, cystoid macular edema, ocular histomplasmosis, ocular toxoplasmosis, retinopathy of prematurity, amblyopia, stabismus, and nystagmus.

As to the subject invention, more specific features and advantages obtained in view of those features will become apparent with reference to the drawing figures and DETAILED DESCRIPTION OF THE INVENTION.

BRIEF DESCRIPTION OF THE DRAWINGS

Referring now to the drawings wherein like numerals are used to designate like parts of the invention throughout the figures.

DETAILED DESCRIPTION OF THE INVENTION

The subject therapy is non-invasive, and involves minimally delivering a precise amount of tightly controlled electrical current through electrodes applied to the skin at specific areas at and/or near the eyes. A multi-frequency pulse generator, e.g., a ScyFIX 600 microcurrent stimulator, commercially available from ScyFIX, LLC of Minnesota, U.S.A., is advantageous for generating direct electrical current between electrodes in furtherance of therapy administration.

Figure 1:
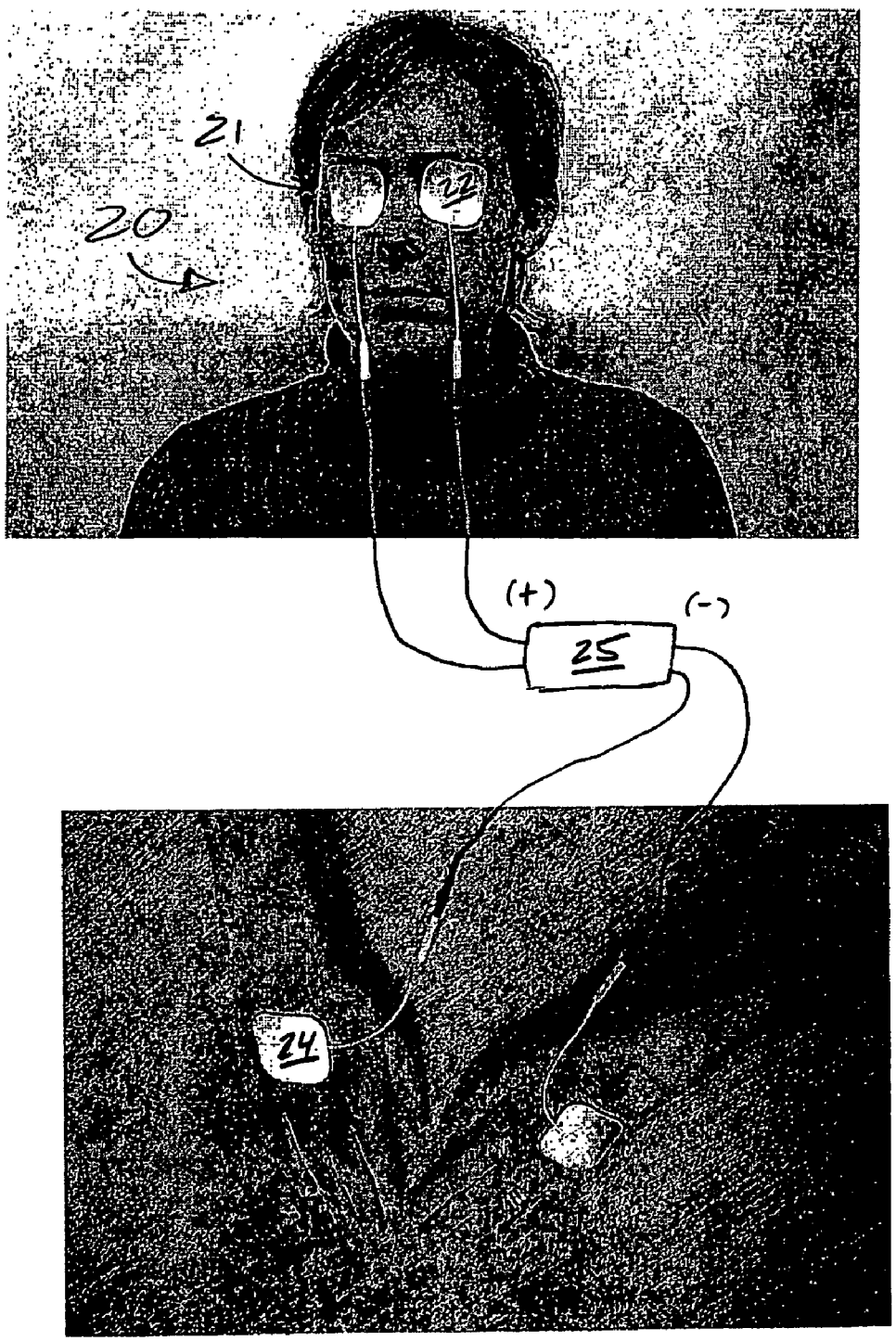
FIG. 1 illustrates a human subject receiving treatment for a vision disorder utilizing the application of microcurrent.
Figure 2:
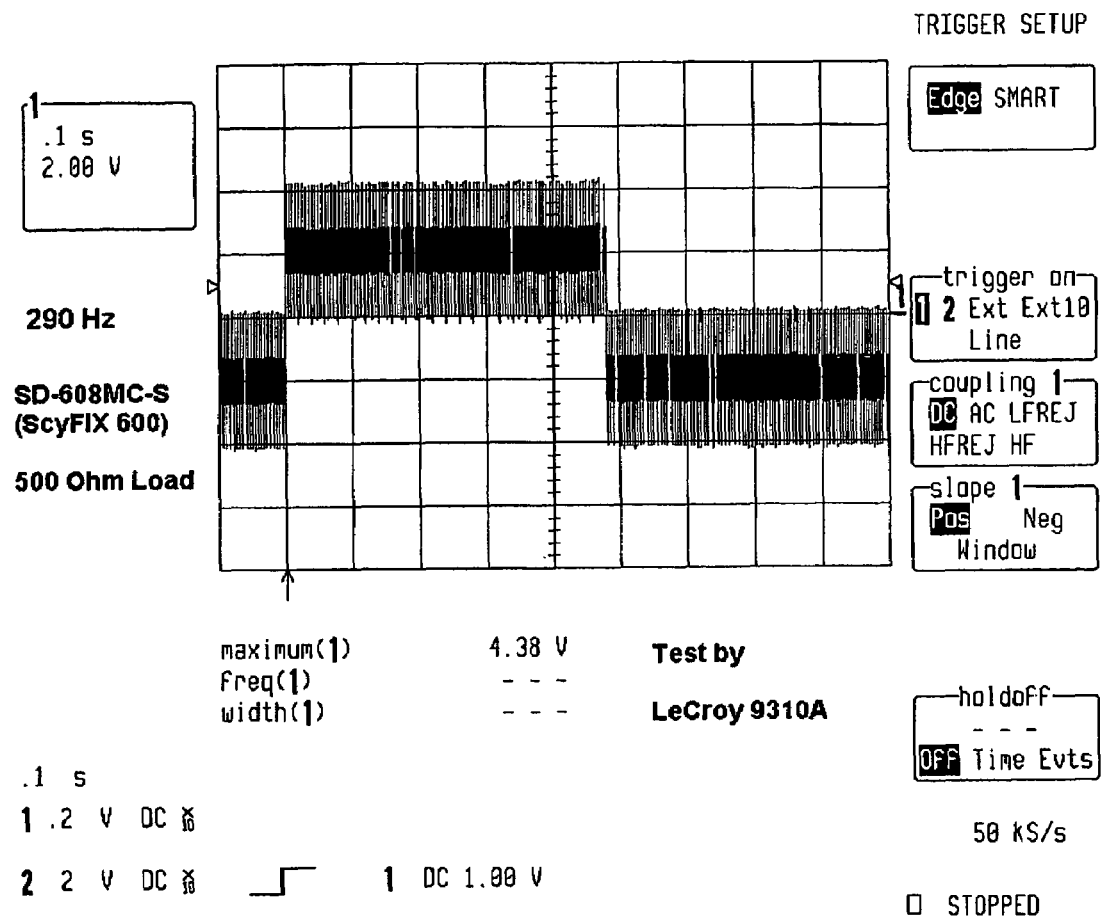
FIGS. 2-5 depict frequency output for each of the preferred sequences of the frequency profile associated with the electrical stimulation of the subject invention.
Figure 3:
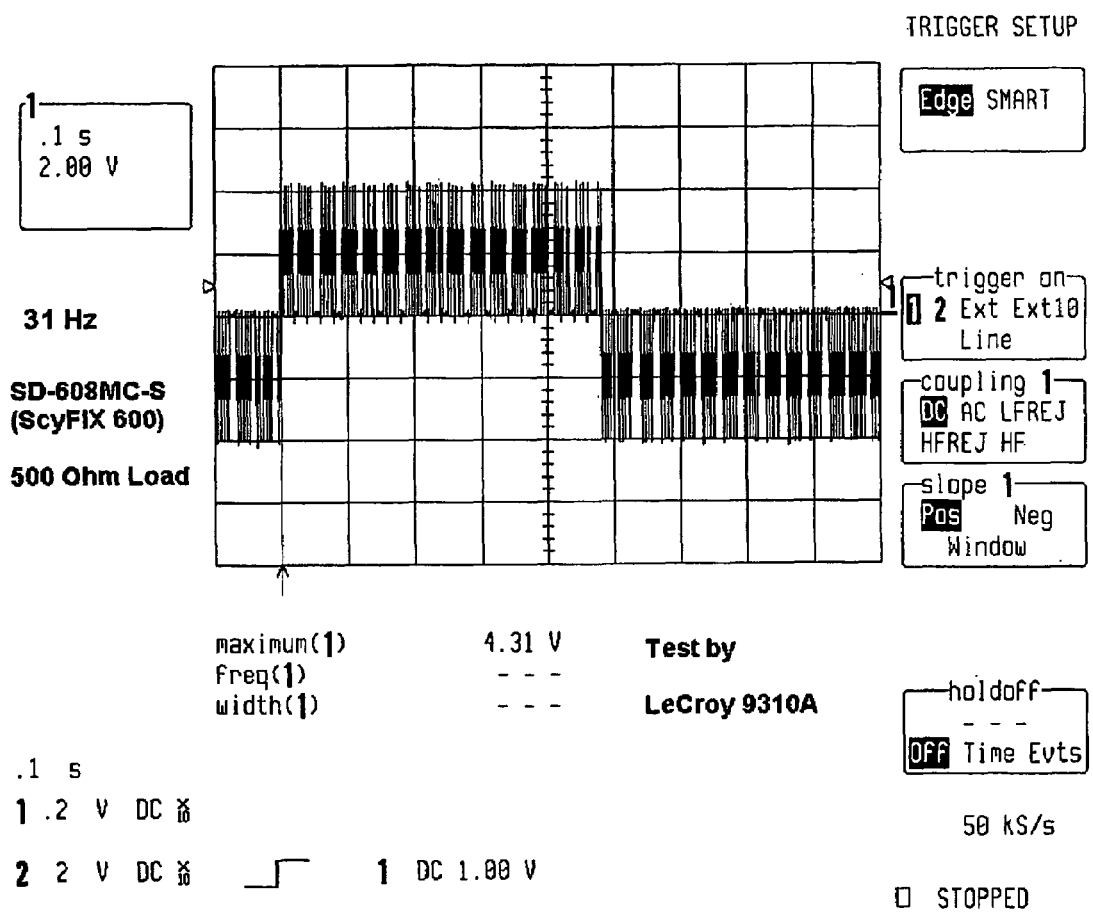
Figure 4:
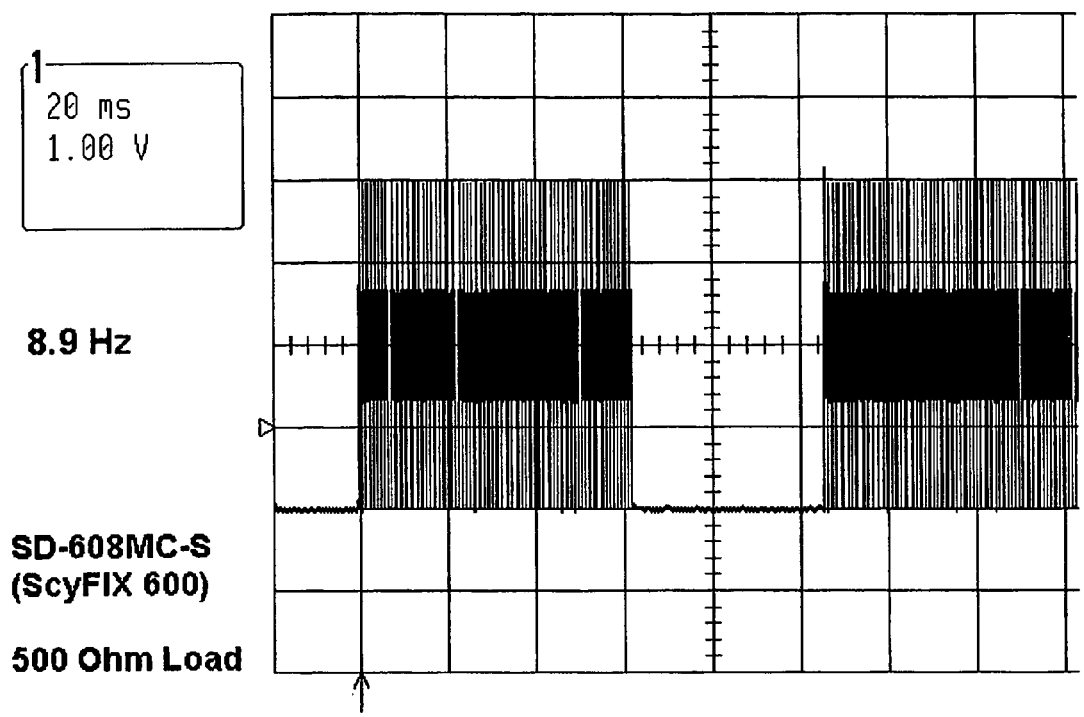
Figure 5:
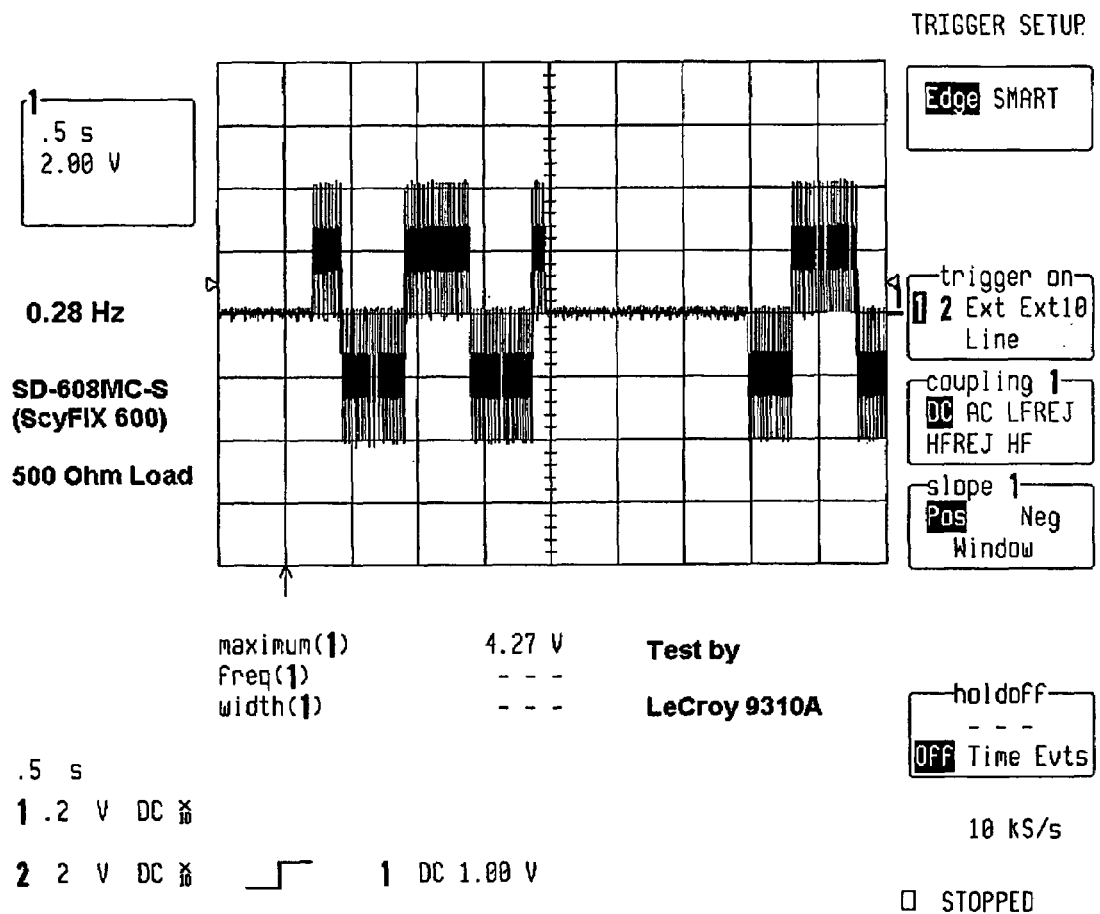
Figure 6:
FIG. 6 is a tabulation of Snellen Chart results for a twelve week study of a plurality of patients undergoing the electrical stimulation of the subject invention; and, FIG. 7-10 illustrate: Snellen acuity, kinetic fields: horizontal effect in degrees; kinetic fields: vertical effect in degrees; and, Humphrey 30-2, total errors data for pre and post treatment subjects undergoing the electrical stimulation of the subject invention.
Figure 7:
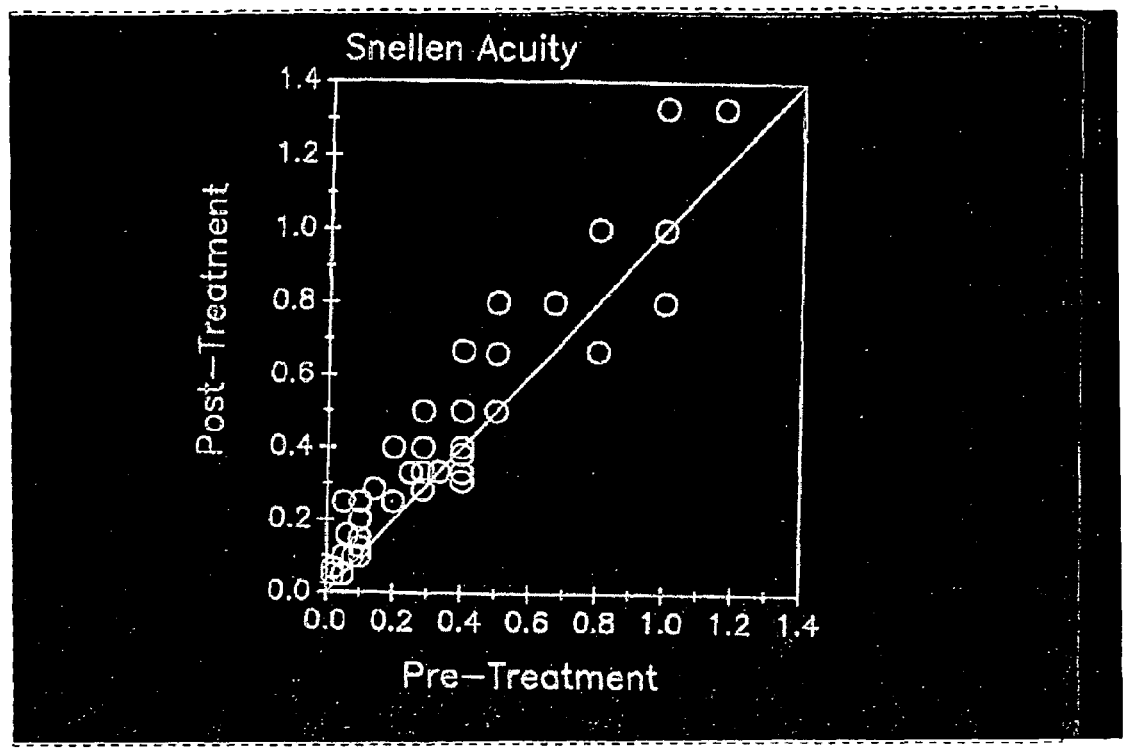
Figure 8:
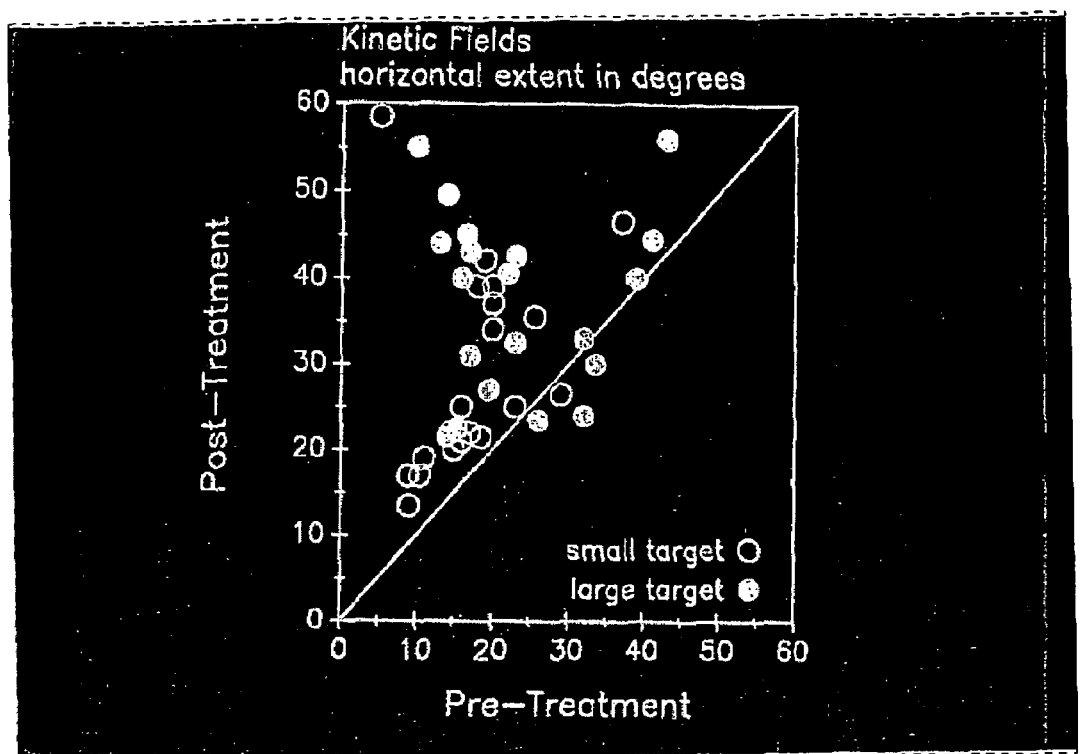
Figure 9:
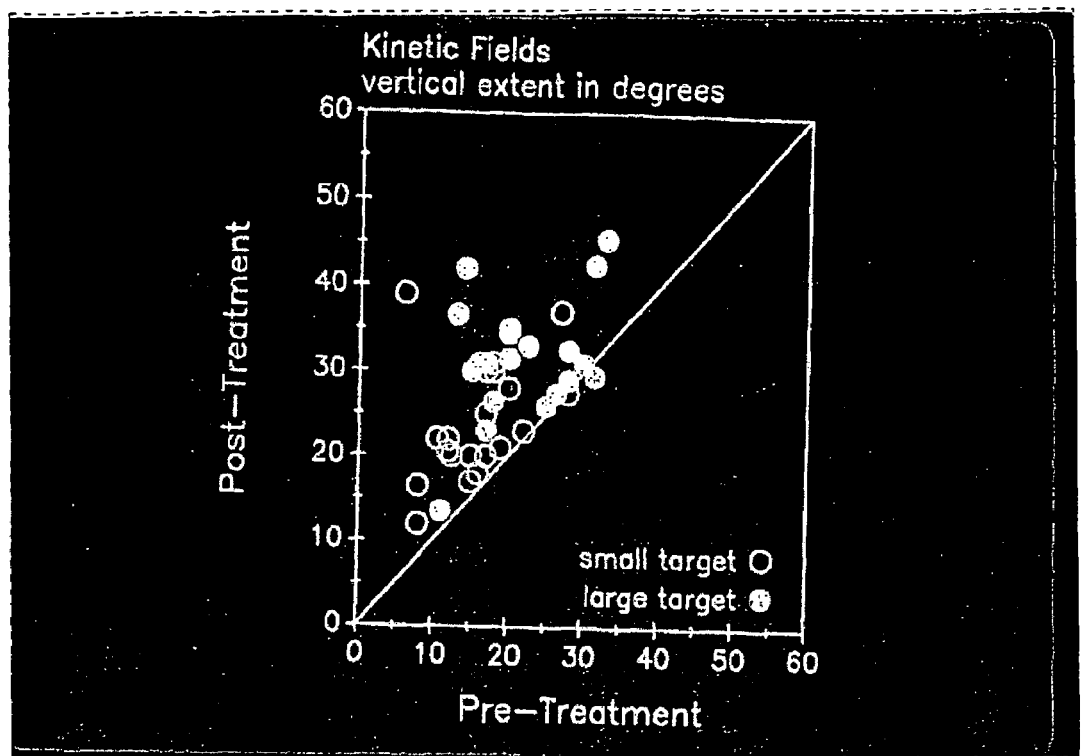
Figure 10:
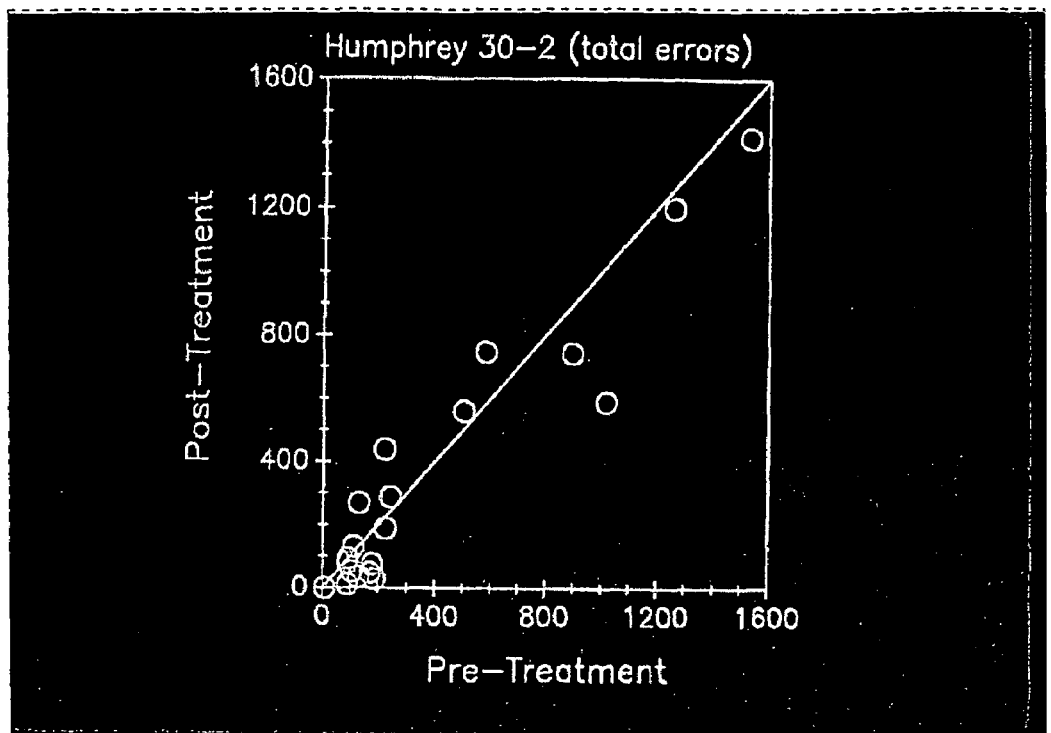

With reference to FIG. 1, there is shown a human subject 20 having at least a single closed lid of an eye 21 in contact with an electrode 22. Electrode 22 is connected to the positive output of a constant current generator 25 having a suitable power source connected thereto or incorporated therein. The negative output of the generator 25 is connected to a second electrode 24, which is preferably attached to the skin at the proximal hand. When the generator 25 is activated, a current loop is established that extends, in order, from the generator 25 through electrode 22 and eye 21 so as to terminate at the second electrode 24. The current loop is completed at the generator 25.

In accordance with one aspect of the invention, a vision disorder, more particularly, a blindness disease in a subject is treated by the steps of: placing a first electrode of a direct current source in electrical contact proximal one or more eyes of a subject, as for example, in contact with a closed eyelid thereof; placing a second electrode of the source in electrical contact with a site remote from the position of the first electrode; and, causing a pulsed direct current from 1 to 800 microamps, at a resistance assumption of about 500 ohms, to flow between the electrodes and through the subject for a preselect duration, e.g., about twenty minutes. In a preferred embodiment, up to four discrete frequencies are utilized in the course of the preselected duration, more particularly, a frequency profile is administered wherein, for example, the frequency profile comprises a sequence of about 290 Hz (i.e., 250-300 Hz) for about one minute; about 31 Hz (i.e., 25-35 Hz) for about two minutes; about 8.9 Hz (7-10 Hz) for either about seven or ten minutes (i.e., at least about seven minutes); and, about 0.28 Hz (i.e., 0.15-0.3 Hz) for either about seven or ten minutes (i.e., at least about seven minutes). Associated frequency output charts for each of the preferred sequences of the profile are depicted in FIGS. 2-5. The employed frequencies are utilized to amplitude modulate a pulsed carrier signal having a pulse frequency of about 10,000-12,000 Hz. Advantageously, the carrier signal is switched on and off in time and inverted about every 0.5 seconds by reversing the polarity of the signal at the electrodes.

With general and passing references to FIGS. 6-10, FIG. 6 is a tabulation of Snellen Chart results for a twelve week study of a plurality of patients undergoing the electrical stimulation of the subject invention. The paired columns represent pre/post treatment Snellen chart results for right (i.e., OD) and left (i.e., OS) eyes. FIGS. 7-10 illustrate: Snellen acuity, kinetic fields: horizontal effect in degrees; kinetic fields: vertical effect in degrees; and, Humphrey 30-2, total errors data for pre and post treatment subjects undergoing the electrical stimulation of the subject invention.

In accordance with another aspect of the therapy of the subject invention, the source is a portable, battery powered constant direct current generator which is affixed/affixable to the subject. The subject is thus enabled to ambulate while the direct current is flowing there-through. In some circumstances, it may be desired that the eyelid not be closed during treatment. In that case, the electrode of the eye may be positioned around the eye. A frame, such as an eyeglass frame or other easily supportable head structure (not shown), may be fitted with an electrode to position and maintain such an electrode about or near the eye.

In an alternate embodiment of non-invasive ocular therapy for vision disorders and the like, light energy is applied to one or both eyes of the subject. Preferably, but not necessarily, light energy is applied at a power density of up to about 4.5 joules per centimeter squared. Furthermore, it appears especially advantageous that the light energy have an optical power of about 5 milliwatts per centimeter squared, with the light energy preferably applied at a frequency of about 145 Hz for up to about fifteen minutes.

It is generally known that certain biochemical conditions in the brain facilitate effective cortical plasticity such that new functions can occur. Neurotransmitters trigger this biochemistry and allow for additional synoptic connections to initiate movement and growth in new directions. Colored light therapy is believed to act as a powerful tool to stimulate the biochemistry of the brain through the visual system by way of the retinal-hypothalamus brain connection.

With regard to apparatus for effectuating heretofore described therapies, an electrode-carrying structure (e.g., a frame, head band or other head gear) may be fitted with known light emitting devices capable of delivering or administering one or more select frequencies. For example, LEDs or IREDs may be employed to provide light energy of a desired frequency dependent upon the particular blindness disease. Blue-green colors are believed useful for macular degeneration, and other blindness diseases, while red-yellow colors are believed useful for retinitus pigmentosis, and related or similar blindness diseases. Particular wavelength ranges that are believed to be useful are: about 450-500 nm (i.e., more generally, "blue"); about 520-570 nm (i.e., more generally, "green"); about 565-590 nm ((i.e., more generally, "yellow"); and, 625-740 nm (i.e., more generally, "red"). Light therapy at, or including, these wavelength ranges may be advantageously employed for blindness disease.

In a specific embodiment of the subject therapy, light energy is conducted upon each eye of the subject sequentially between light energy characterized by first and second wavelength ranges. For example, for macular degeneration, the described "frame" or the like may be fitted to direct blue light into one eye and green light into the other while allowing the "colors" to be switched from one treatment cycle to the next, or during an individual treatment cycle. Such approach, utilizing wavelength ranges associated with red/yellow are believed advantageous in treatment of retinitis pigmantosis.

In addition to the intraocular application of electrical and/or light energy, as described above, it may be additionally beneficial to direct infrasonic sound waves (i.e., those having a frequency generally below 20 Hz) directly into the eye or eyes of the subject. Emitters for such sound waves may be carried by the above described frames, or an adaption thereof. It is believed advantageous, in furtherance of treating vision disorders, to direct infrasonic sound waves into the eye, preferably, but not necessarily, at random frequencies ranging from about 8-14 Hz.

While the principles under which the invention produces its beneficial effects are not fully understood, and without restriction to a particular theory of operation, transocular electrical conduction as practiced in accordance with the invention may restore cellular electrical balance by changing potentials across cell membranes. This may alter the levels of certain ions and molecules toward a desirable equilibrium. Other physiological effects are believed to be produced: reduction of alkalinity proximate the passage of electrical current and the production of low levels of hydrochloric acid; attraction of oxygen to the region; localized vasoconstriction; reduction of local hemorrhage; sedation; increased tonicity of local tissues; antisepsis; production of desirable fibroplasia; and reduced neuromuscular irritability. Stimulation through the eyes also allows access to more then thirty-three percent of the total blood volume of the body in a twenty minute treatment session. The blood consists of many cells which exist to capture electro-magnetic energy to control and direct biomechanical reactions. This also includes animating and mineralizing the blood by adjusting the pH. Also, with blindness disease, diseased, inflamed retinal cells eventually lose cell function. Adenosine triphosphate (ATP) levels drop, protein synthesis drops, the electrical resistance goes up, and cell membrane electrical potential goes down. Basically, the cells seem to go dormant for a time before they die. So, it is believed that, if electrical stimulation is provided to the cells before they die, blood vessel permeability is increased, a more normal cellular electrical potential will be achieved, the ATP levels will increase, and protein synthesis will occur again.

It is to be understood the aforementioned therapeutic aspects of electrical, light and sound energy may be administered independently of each other (i.e., each individually), or in one or more select combinations/permutations thereof. Furthermore, there are other variations of the subject invention, some of which will become obvious to those skilled in the art. It will be understood that this disclosure, in many respects, is only illustrative, and is not intended to be limiting. Accordingly, the scope of the subject invention is as defined in the language of the appended claims.

The invention claimed is:

1. A non-invasive ocular therapy for vision disorders comprising:
   a. positioning a first electrode on or proximate to an eyelid of a subject;
   b. positioning a second electrode on the subject; and
   c. generating an electric current between said electrodes of between 1-800 microamps wherein the electrical current is generated at multiple frequencies and modulated with a carrier signal in a range of about 10,000 hertz to less than 12,000 hertz.

2. The therapy of claim 1 wherein said electrical current is generated at about 292 hertz for about one minute.

3. The therapy of claim 1 wherein said electrical current is generated at about 8-9 hertz for at least seven minutes.

4. The therapy of claim 1 wherein said electrical current is generated at about 0.15-0.3 hertz for at least seven minutes.

5. The therapy of claim 1 wherein said carrier signal is modulated on and off.

6. The therapy of claim 5 wherein said carrier signal is inverted by reversing a polarity thereof at said electrodes.

7. The therapy of claim 6 wherein said carrier signal is inverted about every 0.05 seconds.

8. The therapy of claim 1 further comprising the application of light energy to the eye of the subject at a power density of up to about 4.5 joules per centimeter squared.

9. The therapy of claim 8 wherein said light energy has an optical power of about 5 milliwatts per centimeter squared.

10. The therapy of claim 9 wherein said light energy is applied at a frequency of about 145 hertz for up to about 15 minutes.

11. The therapy of claim 10 wherein said light energy is characterized by wavelength ranges of about 450-500 nanometers, 520-570 nanometers, 565-590 nanometers or 625-740 nanometers.

12. The therapy of claim 11 wherein applying said light energy is conducted upon each eye of the subject sequentially characterized by first and second wavelength ranges.

13. The therapy of claim 12 wherein said first wavelength range is 450-500 nanometers.

14. The therapy of claim 13 wherein said second wavelength range comprises about 520-570 nanometers.

15. The therapy of claim 12 wherein said first wavelength range comprises about 520-570 nanometers.

16. The therapy of claim 15 wherein said second wavelength range comprises about 450-500 nanometers.

17. The therapy of claim 12 wherein said first wavelength range comprises about 565-590 nanometers.

18. The therapy of claim 17 wherein said second wavelength range comprises about 625-740 nanometers.

19. The therapy of claim 12 wherein said first wavelength range comprises about 625-740 nanometers.

20. The therapy of claim 19 wherein said second wavelength range comprises about 565-590 nanometers.

21. The therapy of claim 1 further comprising the application of infrasonic sound waves directly into eyes of the subject.

22. The therapy of claim 21 wherein said infrasonic sound waves are characterized by frequencies from about 8-14 hertz.

23. A non-invasive ocular therapy for vision disorders comprising:
   a. positioning a first electrode on or proximate to an eyelid of a subject;
   b. positioning a second electrode to on the subject; and
   c. generating an electrical current between said electrodes of between 1- 800 microamps wherein said electrical current is generated at a selected frequency profile of multiple frequencies and modulated with a carrier signal of about 10,000 hertz to less than 12,000 hertz.

24. The therapy of claim 23 wherein said frequency profile comprises about 292 hertz for about one minute, about 31 hertz for about 2 minutes, about 8-9 hertz for at least seven minutes, and about 0.15-0.3 hertz for at least seven minutes.

25. The therapy of claim 23 further comprising the application of infrasonic sound waves directly into the eyes of the subject.

26. The therapy of claim 25 wherein said infrasonic sound waves are characterized by frequencies from about 8-14 hertz.

* * * * *